US008903675B2

(12) United States Patent
Jauriqui et al.

(10) Patent No.: US 8,903,675 B2
(45) Date of Patent: Dec. 2, 2014

(54) ACOUSTIC SYSTEMS AND METHODS FOR NONDESTRUCTIVE TESTING OF A PART THROUGH FREQUENCY SWEEPS

(75) Inventors: Leanne Jauriqui, Albuquerque, NM (US); Christopher Dennis Ziomek, Albuquerque, NM (US); Shawn A. Knapp-Kleinsorge, Albuquerque, NM (US); Lemna Hunter, Corrales, NM (US); James J. Schwarz, Albuquerque, NM (US)

(73) Assignee: Vibrant Corporation, Albuquerque, NM (US)

( * ) Notice: Subject to any disclaimer, the term of this patent is extended or adjusted under 35 U.S.C. 154(b) by 451 days.

(21) Appl. No.: 13/274,150

(22) Filed: Oct. 14, 2011

(65) Prior Publication Data
US 2013/0096881 A1  Apr. 18, 2013

(51) Int. Cl.
*G01N 29/46* (2006.01)
*G01N 29/04* (2006.01)
*G01N 29/34* (2006.01)

(52) U.S. Cl.
CPC ............ *G01N 29/043* (2013.01); *G01N 29/348* (2013.01); *G01N 29/46* (2013.01); *G01N 2291/102* (2013.01)
USPC .......................................... 702/124; 702/190

(58) Field of Classification Search
CPC ....... G06F 19/00; E21B 47/00; B06B 1/0284; B06B 1/0276; B06B 1/0618; B06B 1/0269; B06B 1/0614; B06B 9/10; G01V 11/007; G01V 3/38; G01N 29/46; G10K 11/004; G10K 11/343
USPC .......................................... 73/582, 599–657
See application file for complete search history.

(56) References Cited

U.S. PATENT DOCUMENTS

| 2,921,465 | A | * | 1/1960 | Cook ............................... 73/612 |
| 3,404,341 | A | * | 10/1968 | Young .......................... 324/109 |
| 3,454,874 | A | * | 7/1969 | Young .......................... 324/230 |
| 3,628,141 | A | * | 12/1971 | Union et al. ................. 324/72.5 |
| 3,696,369 | A | * | 10/1972 | Laymon et al. ............... 367/136 |
| 4,158,843 | A | * | 6/1979 | Kuchy .......................... 342/448 |
| 4,437,134 | A | * | 3/1984 | Dupraz .......................... 361/56 |
| 4,691,707 | A | * | 9/1987 | Sankar .......................... 600/443 |
| 5,035,144 | A | * | 7/1991 | Aussel ............................. 73/602 |
| 5,062,296 | A | * | 11/1991 | Migliori .......................... 73/579 |
| 5,351,543 | A | * | 10/1994 | Migliori et al. ................. 73/579 |

(Continued)

OTHER PUBLICATIONS

Sean McPeak, Generate a swept sine in LabView, Feb. 2009, Test & Measurement World www.tmworld.com.*

*Primary Examiner* — Eliseo Ramos Feliciano
*Assistant Examiner* — I-Hui E Liu
(74) *Attorney, Agent, or Firm* — James L. Johnson; Marsh Fischmann & Breyfogle LLP

(57) ABSTRACT

A waveform generator and a signal analyzer are respectively provided in electrical communication with an input transducer and an output transducer capable of conversion between electrical and acoustic signals, and in mechanical communication with a part. A processor coupled with the waveform generator and signal analyzer receives a set of parameters defining a frequency scan from which it determines a number of frequency sweeps to be performed by the waveform generator. Each of the frequency sweeps has a number of frequencies less than a maximum capacity of the waveform generator, and for each frequency sweep, the processor instructs the waveform generator to excite the input transducer and synchronously receiving a response signal with the signal analyzer at multiple frequencies.

12 Claims, 5 Drawing Sheets

(56) References Cited

U.S. PATENT DOCUMENTS

| | | | |
|---|---|---|---|
| 5,363,050 A * | 11/1994 | Guo et al. | 324/638 |
| 5,406,503 A * | 4/1995 | Williams et al. | 702/106 |
| 5,408,880 A | 4/1995 | Rhodes et al. | |
| 5,425,272 A * | 6/1995 | Rhodes et al. | 73/579 |
| 5,591,913 A * | 1/1997 | Tucker | 73/628 |
| 5,641,905 A | 6/1997 | Schwarz et al. | |
| 5,770,945 A * | 6/1998 | Constable | 324/350 |
| 5,952,576 A | 9/1999 | Schwarz | |
| 5,992,234 A * | 11/1999 | Rhodes et al. | 73/579 |
| 6,078,184 A * | 6/2000 | Heuermann | 324/755.02 |
| 6,202,490 B1 * | 3/2001 | Taniguchi et al. | 73/628 |
| 6,237,410 B1 * | 5/2001 | Dyck et al. | 73/290 V |
| 6,301,967 B1 * | 10/2001 | Donskoy et al. | 73/579 |
| 6,334,051 B1 * | 12/2001 | Tsurumi et al. | 455/324 |
| 6,418,079 B1 * | 7/2002 | Fleure | 367/40 |
| 6,861,833 B2 | 3/2005 | Miyauchi | |
| 7,307,413 B2 * | 12/2007 | McKim, Jr. | 324/133 |
| 2004/0204034 A1 * | 10/2004 | Hanrahan | 455/552.1 |
| 2005/0140386 A1 * | 6/2005 | Strid et al. | 324/762 |
| 2005/0285600 A1 * | 12/2005 | Bartley et al. | 324/523 |
| 2006/0181281 A1 * | 8/2006 | Moore | 324/338 |
| 2007/0282200 A1 | 12/2007 | Johnson et al. | |
| 2008/0101212 A1 * | 5/2008 | Yu et al. | 370/208 |
| 2008/0257047 A1 | 10/2008 | Pelecanos et al. | |
| 2009/0078049 A1 * | 3/2009 | Sinha | 73/623 |
| 2009/0079424 A1 | 3/2009 | Tralshawala et al. | |
| 2009/0292476 A1 * | 11/2009 | Abma | 702/16 |
| 2010/0191107 A1 | 7/2010 | Bowers et al. | |
| 2010/0244818 A1 * | 9/2010 | Atwood et al. | 324/233 |
| 2011/0080805 A1 * | 4/2011 | Vu et al. | 367/32 |

* cited by examiner

ACOUSTIC SYSTEMS AND METHODS FOR NONDESTRUCTIVE TESTING OF A PART THROUGH FREQUENCY SWEEPS

BACKGROUND OF THE INVENTION

This application relates generally to nondestructive testing of parts. More specifically, this application relates to acoustic systems and methods for nondestructive testing of parts.

There are numerous applications in which it is desirable to identify defects in parts that may have developed through extended use of the part, as a result of damage to the part, as a consequence of natural aging of the part, or as part of a quality-control program during manufacturing processes. Defects frequently take the form of voids or cracks within a part, which may be caused as a result of wear, corrosion, or other processes incidental to use or manufacturing processes. It is preferable that such defects be identified before they are of such magnitude that they will interfere with proper operation of the part or that there is a high risk of breakage or failure of the part.

A variety of techniques have been developed in which parts may be tested "nondestructively," meaning that the testing methodology enables defects to be identified without causing damage to the part. Examples of such nondestructive-testing methodologies include acoustic techniques, magnetic-particle techniques, liquid-penetrant techniques, radiographic techniques, eddy-current testing, and low-coherence interferometry, among others. There are various known advantages and disadvantages to each of these categories of testing methodologies, which are accordingly used in different environments.

Nondestructive-testing methods that use acoustic radiation generally operate in the ultrasonic range of the acoustic spectrum, and are valuable for a number of reasons. Such techniques are sensitive, for example, to both surface and subsurface discontinuities, enabling identification of defects both within the bulk and near the surface of a part. The depth of penetration for defect detection is generally superior to many other nondestructive-testing methodologies, and the techniques are highly accurate not only in determining the position of a defect, but also in estimating its size and shape.

This application is accordingly related to systems and methods for nondestructive testing of parts using acoustic techniques, both in the ultrasonic portion of the acoustic spectrum and in other portions of the spectrum.

SUMMARY

Embodiments of the invention provide systems and methods for nondestructive testing of a part. The methods of the invention may also be embodied in a computer-readable storage medium having a computer-readable program for directing operation of the system.

A waveform generator is provided in electrical communication with an input transducer that is capable of conversion between electrical signals and acoustic signals, and in mechanical communication with the part. A signal analyzer is provided in electrical communication with an output transducer that is similarly capable of conversion between acoustic signals and electrical signals, and in mechanical communication with the part. A processor is in electrical communication with the waveform generator and with the signal analyzer. It receives a set of parameters defining a frequency scan. It determines a number of frequency sweeps to be performed by the waveform generator from the set of parameters, with each of the frequency sweeps having a number of frequencies less than a maximum capacity of the waveform generator. For each of the frequency sweeps, it instructs the waveform generator to perform the frequency sweeps by exciting the input transducer and synchronously receiving a response signal with the signal analyzer at each of a plurality of frequencies. Each of the frequency sweeps includes a frequency in common with another of the frequency sweeps.

In some embodiments, each of the frequency sweeps includes at least 25 frequencies in common with another of the frequency sweeps.

The waveform generator may have an output impedance less than 10Ω. The signal analyzer may have an input impedance greater than 1 kΩ and may have an input impedance less than 10 kΩ.

In some instances, the waveform generator comprises a plurality of waveform generators. The signal analyzer may comprise an intermediate-frequency digitizer and a real-time digital downconverter.

Different embodiments may also use different types of processing on the response signal. For example, in one embodiment, the response signal is converted over a frequency interval to complex data to which a low-pass filter is applied so that a magnitude envelope of the filtered data may be calculated. In another embodiment, a fast Fourier transform is performed on the response signal over a frequency interval.

Different embodiments may also use different types of processing within the waveform generator. For example, in one embodiment, a waveform generator signal of constant magnitude is frequency-swept using a numerically controlled oscillator (NCO). In another embodiment, an arbitrary waveform generator is used to window the magnitude or envelope of the waveform generator signal as it is frequency-swept.

BRIEF DESCRIPTION OF THE DRAWINGS

A further understanding of the nature and advantages of the present invention may be realized by reference to the remaining portions of the specification and the drawings, wherein like reference labels are used through the several drawings to refer to similar components. In some instances, reference labels are followed with a hyphenated sublabel; reference to only the primary portion of the label is intended to refer collectively to all reference labels that have the same primary label but different sublabels.

DETAILED DESCRIPTION OF EXEMPLARY EMBODIMENTS

Embodiments of the invention are directed to systems and methods for nondestructive testing of parts. As used herein, references to "parts" are intended to be construed broadly as referring to any component of any device or article of manufacture, or to a device or article of manufacture itself. Merely by way of example, such parts may be deployed in the aerospace, automobile, manufacturing, transport, medical industries, among many others that will be evident to those of skill in the art. Embodiments of the invention make use of "acoustic" testing techniques, the term intending broadly to encompass the use of mechanical vibrations of any frequency, although it will generally be understood that certain frequency ranges are expected to be more useful for the testing of certain parts than other portions of the spectrum. This is because certain parts have properties, derived from the material from which they are constructed, their shape, and other characteristics, that allow their acoustic response to be more discriminatory at certain spectral ranges than at other portions of the spectrum.

Figure 1:
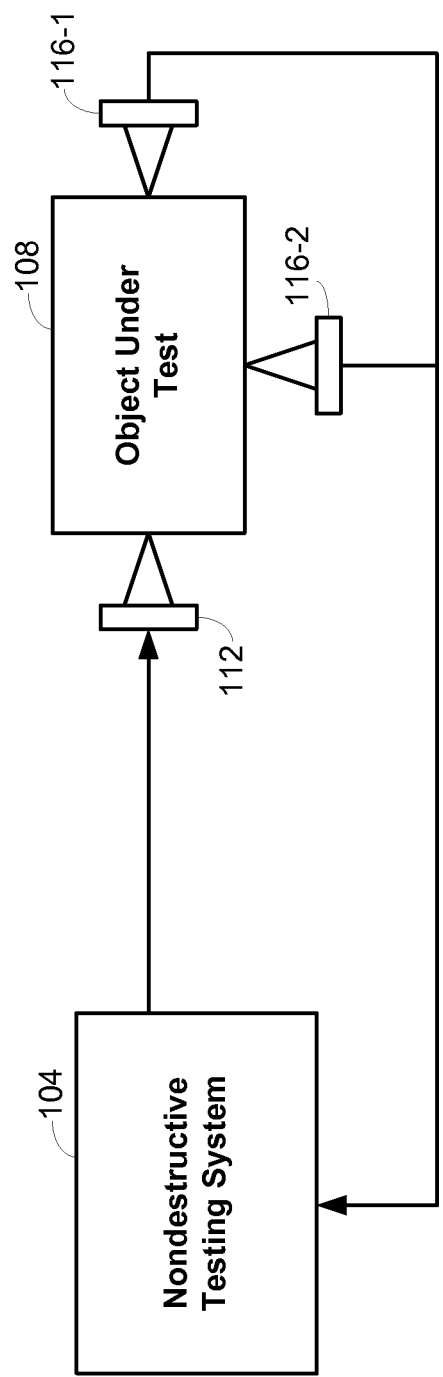
FIG. 1 provides a schematic illustration of a configuration in which systems of the invention may be used.

A broad overview of how parts may be tested nondestructively according to embodiments of the invention is provided with FIG. 1. In this drawing, the part corresponds to an object under test 108 that is provided in mechanical communication with one or more transducers 112 and 116. Each transducer 112 and 116 provides conversion between electrical signals and acoustic vibrations, such as may be provided through the use of crystals or ceramics that have piezoelectric and/or magnetostrictive properties. Examples of such materials include quartz, aluminum nitride, gallium phosphate, and lithium tantalate, among others. Furthermore, the transducers 112 and 116 may be configured for activation in different piezoelectric modes of vibration that include radial, thickness, longitudinal, and shear modes without deviating from the intended scope of the invention. In the particular implementation shown in the drawing, transducer 112 acts as an input transducer so that electrical waveforms generated by the nondestructive testing system 104 are converted to acoustic waves that impinge upon the object under test 108, while transducers 116 act as output transducers so that acoustic waves generated responsively by the object under test 108 are converted into electrical signals that can be studied and analyzed.

While any number of input and output transducers may be used in various embodiments, the use of a plurality of output transducers 116 advantageously allows for both hetero- and homodyne operation of the nondestructive testing system. For example, heterodyne operation may be implemented through the use of multiple different driving frequencies that are mixed additively or subtractively, while homodyne operation may be implemented through the use of multiple signals at the same frequency.

While not shown explicitly in FIG. 1, the system may include a variety of additional components used in managing the strength and flow of electrical signals to and from the transducers. Such components may include, for instance, electrical amplifiers, filters, analog-to-digital converters, and the like, as understood by those of skill in the art.

The nondestructive testing system 104 is broadly used by scanning through a range of driving frequencies that are applied through the input transducer 112 to the object under test 108 in order to generate a response spectrum that provides an intensity of acoustic response as a function of frequency. While the entire spectrum may, in principle, contain information relevant to the identification of defects, the most useful information is generally to be found in the size and shape of resonance peaks within the acoustic response spectrum. Quantification of properties of the resonance peaks allows for the identification of defects and thereby to discriminate between parts that are acceptable or unacceptable based on such criteria as the size, position, and shape of identified defects. A further description of how such analysis may proceed is provided, for example, in U.S. Prov. Pat. Appl. No. 61/405,573, entitled "UTILIZING RESONANCE INSPECTION OF IN-SERVICE PARTS," filed Oct. 21, 2010 by Lemna J. Hunter et al., the entire disclosure of which is incorporated herein by reference for all purposes.

Figure 2A:
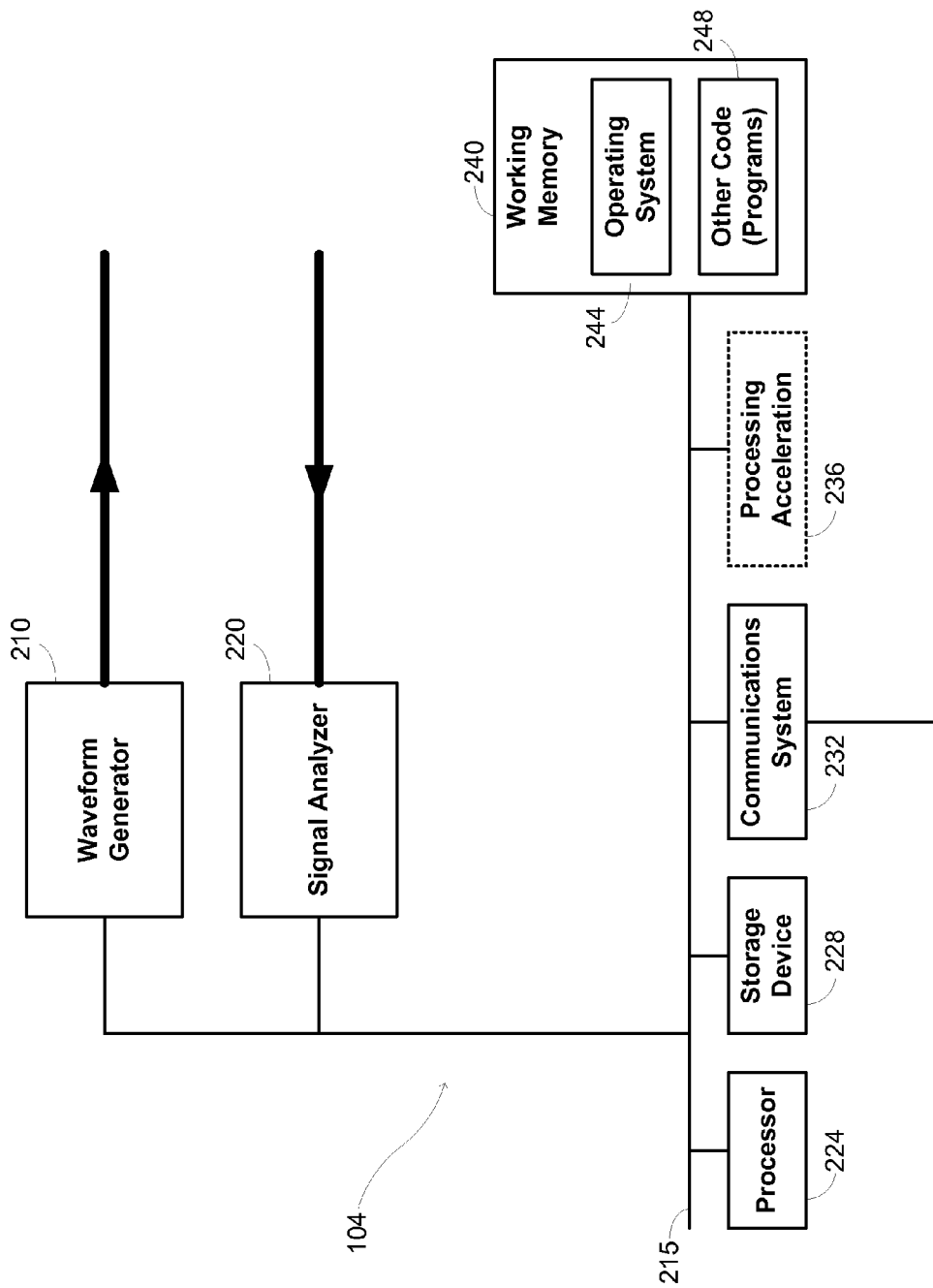
FIG. 2A is a schematic illustration of a structure for a nondestructive testing system in accordance with embodiments of the invention.

FIG. 2A provides a more detailed illustration of a structure for the nondestructive testing system 104 according to an embodiment of the invention. A waveform generator 210 and a signal analyzer 220 are electrically coupled with the bus 215 of a computational unit embodied by the nondestructive testing system 104. In some embodiments, all of these components are advantageously housed within a common structure, but this is not a requirement of the invention and alternative embodiments may use configurations that exploit communications with a remotely situated computational unit.

The waveform generator 210 is generally capable of producing waveforms over a frequency range sufficiently large that it encompasses a large number of smaller sets of frequency ranges that are each suitable for the acoustic testing of a variety of different kinds of parts. Merely by way of example, in one embodiment, the waveform generator 210 is capable of generating excitations over a frequency range of dc-50 MHz, which may encompass such smaller frequency ranges as 100-200 kHz, 50-100 kHz, 75-150 kHz, etc., each of which may represent a suitable acoustic-spectrum sampling to provide the level of discrimination needed for different part types. The determination of which of the smaller sets of frequency ranges is to be used for a particular test may be defined by a number of input parameters that define the characteristics of a sweep through a portion of the acoustic spectrum. One example is a set of input parameters that includes specification of endpoint frequency values, the number of frequencies to be excited over the range between endpoint frequency values, and a duration of each frequency excitation, although it will be appreciated that other input parameters may also uniquely identify the desired spectral range and sweep characteristics. Another example is shaping of the waveform signal magnitude or envelope using an arbitrary waveform generator, such as by synchronizing of windowing shapes to eliminate transient ring-up or ring-down.

The signal analyzer may comprise a digital signal analyzer used for measuring the power of signals generated by the output transducers 116. The signal analyzer 220 may be capable of various forms of analysis of the response spectra to provide a discriminatory characterization that allows classification of the object under test as acceptable or unacceptable. Merely by way of example, spectral analysis performed by the signal analyzer 220 may be used to identify dominant frequencies within the response spectrum, power, distortion, harmonics, and bandwidth of resonances, as well as other spectral components of the signal. In some embodiments, the signal analyzer 220 includes a realtime digital downconverter for converting a digitized real signal at an intermediate frequency to a basebanded complex signal centered at zero frequency. In addition to such downconversion, the signal analyzer 220 may be configured for decimating to a lower sampling rate, thereby allowing improved signal processing. In particular embodiments, the digital downconverter is configured to perform such operations as shifting frequencies, applying filters, and implementing resampling in accordance with defined parameters, resulting in less data to be transferred across bus 215.

To ensure adequate power transfer from the waveform generator 210 and the signal analyzer 220, input and output electrical impedances may be customized according to characteristics of the individual hardware components. The inventors have observed that when the waveform-generator output impedance is as high as 50Ω, for example, relatively little of the power is transferred to the input transducer 112 at higher frequencies. Accordingly, in some embodiments the waveform-generator output impedance is constrained to be less than 50Ω, less than 40Ω, less than 30Ω, less than 20Ω, less than 10Ω, less than 2Ω, or less than 1Ω. Similarly, the inventors have observed that when the signal-analyzer input impedance is as low as 50Ω, relatively little of the power is transferred from the output transducers 116 to the signal analyzer 220 at low frequencies. Accordingly, in some embodiments the signal-analyzer input impedance is greater than 100Ω, greater than 500Ω, greater than 1 kΩ, greater than 2 kΩ, greater than 3 kΩ, greater than 4 kΩ, or greater than 5 kΩ. A signal-analyzer input impedance of about 10 kΩ provides particularly good signal-to-noise performance, with values of that impedance greater than 10 kΩ tending to exhibit excessive signal noise. This represents a tradeoff between loading of low resistance on the transducer and thermal noise of a large resistive element.

Both the waveform generator 210 and the signal analyzer 220 are coupled electronically with elements of the computational unit that aids both in generating excitation signals and in processing response signals. In particular, hardware elements of such a computational unit may be electrically connected with each other and with the waveform generator 210 and the signal analyzer 220 via bus 215. They may include a processor 224, a storage device 228, a processing acceleration unit 236 such as a DSP or special-purpose processor, and a memory 240. A communications system 232 may additionally be provided as a mechanism for interfacing with a user or operator. The communications system 232 may comprise a wired, wireless, modem, and/or other type of interfacing connection and permits data to be exchanged with the nondestructive testing system 104.

Software elements are shown as being currently located within working memory 240, including an operating system 244 and other code 248, such as a program designed to implement methods of the invention. It will be apparent to those skilled in the art that substantial variations may be used in accordance with specific requirements. For example, customized hardware might also be used and/or particular elements might be implemented in hardware, software (including portable software, such as applets), or both. Further, connection to other computing devices such as network input/output devices may be employed.

Figure 2B:
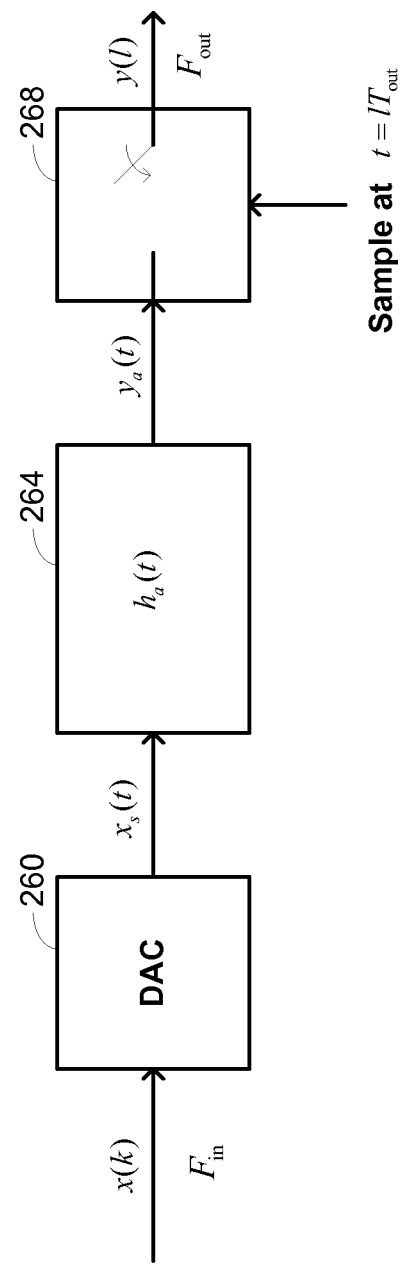
FIG. 2B is a schematic illustration of a continuous-time model for sample rate conversion.

Merely by way of example, sample-rate conversion may be implemented as illustrated in FIG. 2B in a continuous-time model. Input signal x(k) has a sample rate $F_{in}$ and corresponding sample period $T_{in}$ (for the sake of adding clarity to the mathematical operations below, input signal x(k) is shown explicitly as a function of its sampling period, as "$x(kT_{in})$"). Input samples are reconstructed to form the continuous-time signal $y_a(t)$, which is then resampled at the desired time instants. The samples to be reconstructed are input to a digital-to-analog converter 260, followed by filtering with a continuous-time reconstruction filter $h_a(t)$ 264. The output of the digital-to-analog converter 260 is the impulse train given by $$x_s(t) = \sum_{k=-\infty}^{\infty} x(kT_{in})\delta_a(t - kT_{in}),$$

where $\delta_a(t)$ is the Dirac delta function. The continuous-time output of the filter is given by $$y_a(t) = \int_{-\infty}^{\infty} x_s(\lambda)h_a(t - \lambda)d\lambda$$

$$= \sum_{k=-\infty}^{\infty} x(kT_{in})\int_{-\infty}^{\infty} \delta_a(\lambda - kT_{in})h_a(t - \lambda)d\lambda$$

$$= \sum_{k=-\infty}^{\infty} x(kT_{in})h_a(t - kT_{in}).$$

The continuous-time signal may then be resampled at the desired times $t=lT_{out}$ at block 268 yielding the discrete-time signal output $$y(lT_{out}) = \sum_{k=-\infty}^{\infty} x(kT_{in})h_a(lT_{out} - kT_{in}).$$

This result shows that the computation of the discrete-time signal output $y(lT_{out})$ is a function of the resampled output signal $x(kT_{in})$, and samples from the continuous-time impulse response $h_a(T)$ (as with the input signal above, for the sake of adding clarity to the mathematical operations, output signal y(l) is shown explicitly as a function of its sampling period, as "$y(lT_{out})$"). With a continuous-time filter such that its samples can be readily computed, the entire operation may take place in the discrete-time domain.

Figure 3:
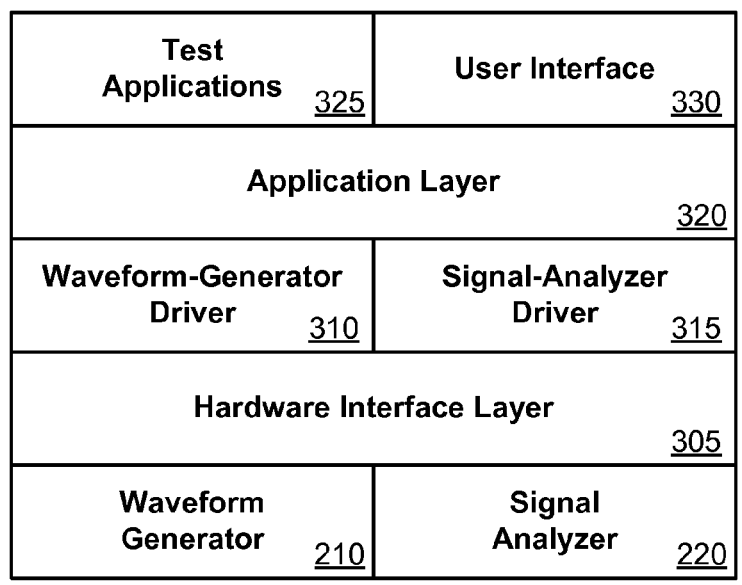
FIG. 3 illustrates a layered software structure that may be used by the nondestructive testing system of FIG. 2A.

A structural overview of software used to manage operation of the nondestructive testing system 104 is shown schematically in FIG. 3 as a layered structure, with different software modules being structure to interact with other modules according to the layer in which they appear in the structure. At the lowest layer is a hardware interface layer 305 that acts as a common driver interface with both the waveform generator 210 and the signal analyzer 220 and that provides a common interface for the application-specific drivers 310 and 315. With the layered software structure, the waveform-generator driver 310 and the signal-analyzer driver 315 may be more broadly structured to provide functionality for classes of waveform generators and for classes of signal analyzers respectively, rather than being configured for the specific characteristics of the specific waveform generator 210 and signal analyzer 220 used in a particular embodiment. This is enabled by the fact that different hardware interfaces may nonetheless use the same signal forms so that the software configurations may be established at this layer. It generally permits the nondestructive testing system 104 as a whole to be configured for relatively easy substitution of the waveform generator 210 and signal analyzer 220, such as may be desirable for specialized applications or to implement improvements in the functionality of the waveform generator 210 and signal analyzer 220. These platform drivers 310 and 315 may thus be configured to perform such functions as initializing the waveform generator 210 and signal analyzer 220, resetting the waveform generator 210 and signal analyzer 220, setting voltage levels, and the like.

An application layer 320 interfaces with the platform drivers 310 and 315 and is responsible for overseeing and coordinating the general operations of the nondestructive testing system 104, including issuing instructions for configuration of the hardware layers 210 and 220, for managing the frequency sweeps, and for processing data that are received from the output transducers 116. It may interact with test applications 325 and a user interface 330 through which the input parameters may be provided by an external user or operator. The user interface 330 may comprise a graphical user interface in particular embodiments. In addition, the application layer 320 effects a synchronization between the waveform generator 210 and the signal analyzer 220 so that analysis of response signals is robust.

Figure 4:
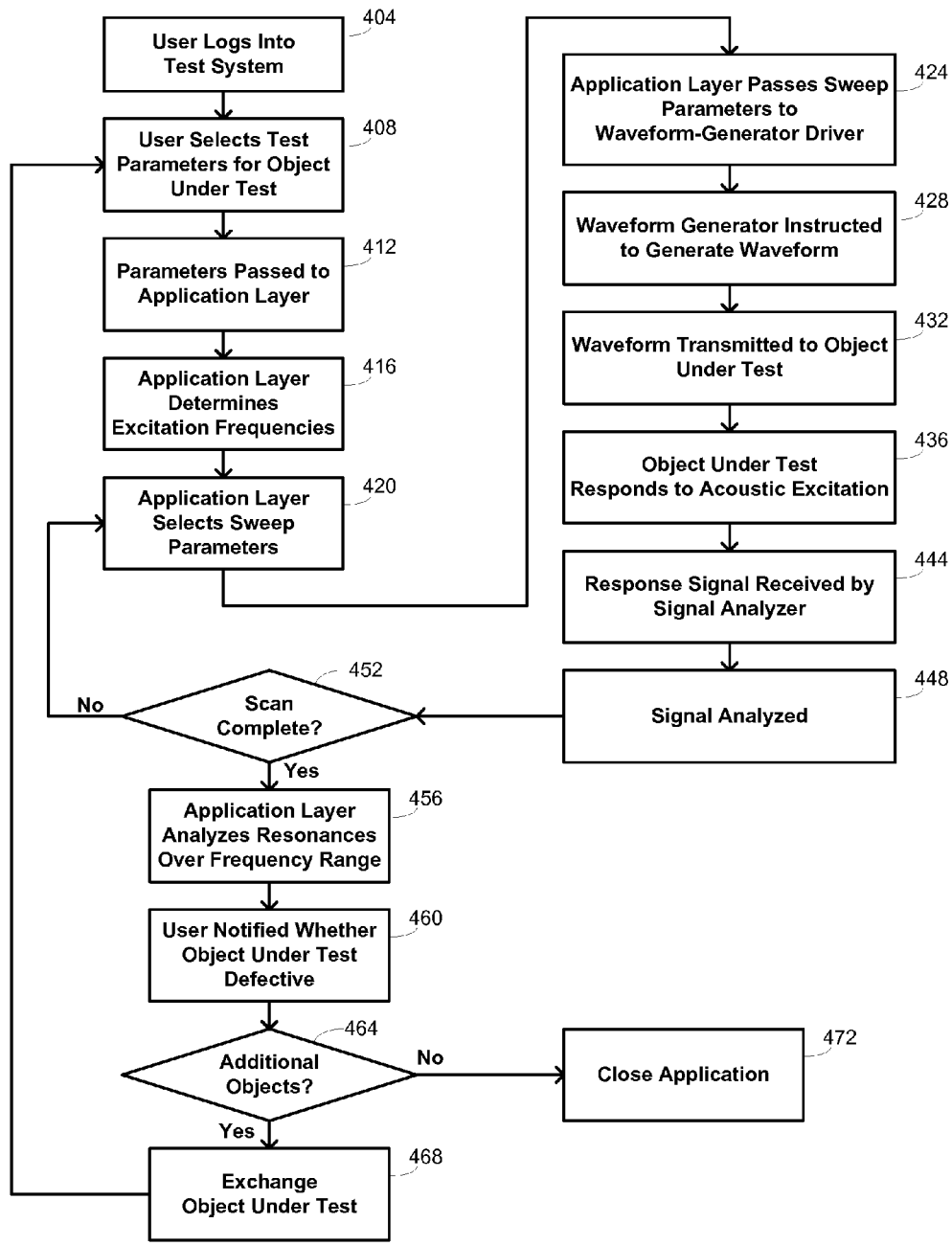
FIG. 4 is a flow diagram summarizing methods of using the nondestructive testing system of FIG. 1.

In some embodiments, the application layer 320 may be configured with four broad levels of functionality that include an initialization function, a setup function, a sweep function, and a close function. The initialization function operates to open a communication session with both the waveform generator 210 and the signal analyzer 220, to allocate memory, verify links, and the like. It is usually called only a single time during a testing session, even if that testing session may involve the testing of a plurality of parts. The setup function acts to prepare the waveform generator 210 and signal analyzer 220 for a frequency sweep, through the communication session opened by the initialization function, and the sweep function implements the sweep in accordance with user-specified parameters. The setup and sweep functions may be called multiple times, such as may be the case when a testing session involves the testing of multiple parts. The close function performs the converse of the initialization function by closing the communication session and freeing up any memory and other resources that were allocated to perform the test. The specific operational functionality of these different functions may be understood more fully in the context of the method by which parts are tested as outlined by the flow diagram of FIG. 4 below.

This flow diagram provides a general overview of methods for performing nondestructive tests of parts in accordance with embodiments of the invention. While the flow diagram sets forth a number of specific steps to be performed, and provides an illustrative ordering of those steps, it should be understood that this is not intended to be limiting. More generally, certain steps that are explicitly called out may be omitted in some embodiments, additional steps that are not explicitly called out may be performed in some embodiments, and the ordering of the steps may be varied in some embodiments.

Methods of testing a part begin at block 404 when a user or operator logs into the test system, enabling the user to select test parameters for the object under test at block 408. Such test parameters are intended to define a frequency scan to be implemented with the sweep function of the application layer 320. As used herein, a frequency "sweep" refers to a progressive excitation of frequencies by the waveform generator 210 consistent with any limitations on the number of excitations that may be generated during a single session by the waveform generator 210, while a frequency "scan" refers to a progressive excitation of frequencies without such limitations. As such, a frequency scan may comprise a plurality of frequency sweeps when the number of frequencies to be excited exceeds the capacity of the waveform generator 210 for a single session (or may comprise a plurality of frequency sweeps when the there are other reasons to prefer having the scan effected in parts). Any combination of parameters may be used from which the frequencies of each excitation along the scan may be determined, one example of which is to request that the user provide endpoint values for the frequency range of the scan, the number of points to be used, and the dwell time of excitation at each frequency. In some instances, the input parameters are selected by the user from a menu of potential values while in other instances the input parameters are provided freeform by the user. At block 412, the input parameters are passed from the user interface 330 to the application layer 320, which may accordingly execute its initialization function to prepare the other components of the system and to open the communication channel.

At block 416, the application layer 320 determines the excitation frequencies to be used. In some cases, this determination may be straightforward, such as in embodiments where the user has provided parameters generally in the form to be used by the waveform generator so that calculation of specific excitation frequencies is simply arithmetic. In other instances, such as where the waveform generator 210 anticipates a specification of wavelengths rather than frequencies or where some other incompatibility exists between the form of parameter specification, the application layer may effect an appropriate conversion. Also, in some instances, the waveform generator may have operational limits that are inconsistent with the input parameters, such as in those embodiments noted above where the desired number of excitation frequencies exceeds an operational limit to the number of frequency steps the waveform generator 210 is capable of. In such embodiments, the software may be configured to operate the waveform generator 210 in a manner consistent with its operational limits by directing it to implement multiple sweeps, each of which is independently consistent with such operational limits. For instance, if the waveform generator is capable of exciting no more than 1000 frequencies during a sweep and the input parameters require a scan that has 5000 frequencies, the software may define multiple sweeps, each of which includes fewer than 1000 frequencies, and may manage the resulting data to mimic the implementation of a single scan with the 5000 frequencies. Such techniques may use sweep-by-sweep backtracking and waveform overlap, with the interaction between the waveform generator 210 and software thereby overcoming inherent limitations in the capacity of the waveform generator 210. In addition, a certain number of frequencies may be allocated as pre-charge frequencies. This provides a preliminary mode of operation for the waveform generator 210 to reduce power-up stress.

In alternative embodiments, backtracking may be avoided through the use of a shaped magnitude. A phase-continuous sweep may be used to eliminate transients that excite broad frequencies, such as may be achieved through the use of a numerically controlled oscillator. In other alternative embodiments, an analog frequency sweep may be implemented instead of using discrete steps.

Thus, once the application layer 320 has determined the frequencies to be used in testing a part, the setup function is initiated so that the waveform generator 210 and signal analyzer 220 may be prepared into a state to effect frequency sweeps. In addition, the setup function calculates how many and which sweeps are required to effect a full scan over the desired frequency range, as well as how long the entire scan will take. For a first frequency sweep, sweep parameters are selected at block 420 and passed by the application layer 320 to the waveform-generator driver 310 at block 424.

The waveform generator 210 is instructed to generate the appropriate waveforms by the sweep function at block 428 and to transmit those waveforms to the object under test at block 432. For each frequency in the sweep, the input transducer 112 is activated, resulting in acoustic vibration at that frequency by the object under test 108 at block 432. The manner in which the object under test 108 responds at block 436 depends on such characteristics as the structure of the object under test 108 and its composition, particularly responding differently when defects are present because of the effect of such defects in producing local inhomogeneities of the structure. Effectively, the incident waveform undergoes a transformation through interaction with the object under test 108 that results in a response waveform detected by the output transducers 116 so that a response signal is received by the signal analyzer at block 444.

There are a number of different types of sweeps that may be used in different embodiments, including peak detection, fast Fourier transform analysis, and others. The inventors have found that fast Fourier transform analysis is less dependent on dwell and step parameters than peak detection, and does not experience ringdown to the same degree.

It is also noted that the waveform generator 210 may, in some embodiments, comprise a plurality of waveform generators, with the outputs of the plurality of waveform generators thereby creating a differential drive. Considerations that may be involved in using a plurality of waveform generators include the effective multiplicative factor on drive voltage from the use of multiple waveform generators so that the signal-to-noise ratio may be increased, as well as multiplicatively greater costs associated with using multiple drive channels and the cost of special cabling.

In some instances, the signal may be analyzed by the signal analyzer at block 448 to generate intermediate results, but more usually a full analysis will be deferred until all sweeps that make up the full scan have been completed. This is indicated in the flow diagram by checking at block 452 whether the scan has been completed, i.e. whether all of the frequencies determined at block 416 have been used. If not, a further sweep is performed in the same manner by the application layer 320 selecting sweep parameters at block 420 for a subsequent sweep. When multiple sweeps are used in this way to effect the full scan of the object under test 108, the application layer 320 may apply sweep-by-sweep backtracking and waveform overlap. In some embodiments, the backtracking is performed with a fixed number of backtrack steps, such as 10 steps, 20 steps, 30 steps, 40 steps, 50 steps, 75 steps, 100 steps, or some other fixed number. The inventors have found that a uniform backtrack of 50 steps is empirically sufficient to avoid waveform discontinuities. In other embodiments, the backtracking may be performed with a variable number of steps.

Once all sweeps have been completed, the signal analyzer returns a spectrum of the total response to the application layer 320 at block 456 so that the spectrum may be analyzed to determine whether the part is acceptable or unacceptable. In some embodiments, the signal analyzer 220 may return complex data (IQ) so that the magnitude and average of multiple points may be taken per frequency to generate a single output sample. In particular, the application layer 320 perform a software downconversion and converts the data collected by the signal analyzer 220 to complex data, which are low-pass filtered for calculation of the magnitude envelope. This processing may be desirable because the received signals from the output transducers 116 are band-pass signals, and the relative bandwidth of the transducers is generally less than 100%, more usually on the order of 50-70%. Nyquist sampling requires that a signal be sampled at a rate twice the frequency of the highest component of the signal in order to get a unique representation of its frequency content. As known to those of skill in the art, IQ demodulation, which is a complex base-band modulation technique with bandwidth reduction, thereby allows for reduction of the amount of data without loss of essential information. Complex data also allows the phase shift of the signal to be computed. As a part goes through resonance, it experiences a 180° phase shift.pb While all parts of the response spectrum potentially include useful information, the most useful information is generally expected to be found in the location and shape of resonances within the spectrum, as explained more fully in U.S. Prov. Pat. Appl. No. 61/405,573. The user is notified of the determination whether the part is acceptable or unacceptable at block 460.

Since the software of the application layer 320 is structured so that multiple calls of the setup and sweep functions are permitted, the capacity exists to test additional objects, as checked at block 464. If there are additional parts to be tested, the part may be exchanged at block 468, with the process repeating until all parts have been tested. At that point, the close function is used at block 472 to close the communication channel that was opened at block 412 and to free up allocated memory and other resources.

Having described several embodiments, it will be recognized by those of skill in the art that various modifications, alternative constructions, and equivalents may be used without departing from the spirit of the invention. Accordingly, the above description should not be taken as limiting the scope of the invention, which is defined in the following claims.

What is claimed is:

1. A system for nondestructive testing of a part, the system comprising:
    a waveform generator in electrical communication with an input transducer, the input transducer capable of conversion between electrical signals and acoustic signals;
    a signal analyzer in electrical communication with an output transducer, the output transducer capable of conversion between acoustic signals and electrical signals; and
    a processor in electrical communication with the waveform generator and with the signal analyzer, wherein the processor comprises:
        instructions to receive a set of parameters defining a frequency scan including a number of drive frequencies;
        instructions to determine that the number of drive frequencies exceeds a maximum capacity of the waveform generator, the maximum capacity corresponding to a maximum number of frequencies permitted by the waveform generator to be used in defining the frequency scan;
        instructions to determine a number of frequency sweeps to be performed by the waveform generator from the set of parameters, such that each of the frequency sweeps has a number of frequencies that is less than the maximum capacity of the waveform generator and comprises a portion of the drive frequencies, each of the frequency sweeps includes a frequency in common with another of the frequency sweeps, and the frequency sweeps collectively provide the number of drive frequencies; and
        instructions to instruct the waveform generator to perform each of the frequency sweeps by exciting the input transducer and to instruct the signal analyzer to synchronously receive corresponding response signals.

2. The system recited in claim 1 wherein each of the frequency sweeps includes at least 25 frequencies in common with the another of the frequency sweeps.

3. The system recited in claim 1 wherein the waveform generator has an output impedance less than 10 Ω.

4. The system recited in claim 1 wherein the signal analyzer has an input impedance greater than 1 kΩ.

5. The system recited in claim 4 wherein the input impedance is less than 10 kΩ.

6. The system recited in claim 1 wherein the signal analyzer comprises an intermediate-frequency digitizer and a real-time digital downconverter.

7. The system recited in claim 1 wherein the processor further comprises:
    instructions to convert the response signal over a frequency interval to complex data;

instructions to apply a low-pass filter to the complex data; and instructions to calculate a magnitude envelope of the filtered data.

8. The system recited in claim 1 wherein the processor further comprises instructions to perform a fast Fourier transform on the response signal over a frequency interval.

9. A method for nondestructive testing of a part, the method comprising:

receiving a set of parameters defining a frequency scan including a number of drive frequencies;

determining that the number of drive frequencies exceeds a maximum capacity of a waveform generator, the maximum capacity corresponding to a maximum number of frequencies permitted by the waveform generator to be used in defining the frequency scan;

determining, from the set of parameters, a number of frequency sweeps to be performed by the waveform generator in electrical communication with an input transducer capable of conversion between electrical signals and acoustic signals and in communication with the part, so that each of the frequency sweeps has a number of frequencies that is less than the maximum capacity of the waveform generator and comprises a portion of the drive frequencies, each of the frequency sweeps includes a frequency in common with another of the frequency sweeps, and the frequency sweeps collectively provide the number of drive frequencies;

instructing the waveform generator to perform each of the frequency sweeps by exciting the input transducer; and instructing the signal analyzer synchronously to receive a corresponding response signal.

10. The method recited in claim 9 wherein each of the frequency sweeps includes at least 25 frequencies in common with the another of the frequency sweeps.

11. The method recited in claim 9 further comprising:

converting the response signal over a frequency interval to complex data;

applying a low-pass filter to the complex data; and calculating a magnitude envelope of the filtered data.

12. The method recited in claim 9 further comprising performing a fast Fourier transform on the response signal over a frequency interval.

\* \* \* \* \*